United States Patent
Watson et al.

(10) Patent No.: US 8,845,626 B2
(45) Date of Patent: Sep. 30, 2014

(54) LENSED DUAL-CHIP FIBER-COUPLER FOR PROVIDING AN AIMING BEAM IN AN INFRARED RADIATION DELIVERY APPARATUS

(75) Inventors: Jason P. Watson, San Jose, CA (US); David Schleuning, Oakland, CA (US)

(73) Assignee: Coherent, Inc., Santa Clara, CA (US)

( * ) Notice: Subject to any disclaimer, the term of this patent is extended or adjusted under 35 U.S.C. 154(b) by 1238 days.

(21) Appl. No.: 12/571,669

(22) Filed: Oct. 1, 2009

(65) Prior Publication Data
US 2011/0082447 A1    Apr. 7, 2011

(51) Int. Cl.
*A61B 18/18* (2006.01)
*G02B 6/32* (2006.01)
*G02B 6/255* (2006.01)
*A61B 17/00* (2006.01)
*A61B 18/22* (2006.01)

(52) U.S. Cl.
CPC ..................................... *A61B 18/22* (2013.01)
USPC ........................ 606/16; 385/33; 385/93; 606/1

(58) Field of Classification Search
USPC ............... 359/19; 606/16; 362/259, 553, 554, 362/556; 385/93, 33; 398/44, 143, 172
See application file for complete search history.

(56) References Cited

U.S. PATENT DOCUMENTS

| | | | | |
|---|---|---|---|---|
| 4,714,314 A * | 12/1987 | Yang et al. | | 385/42 |
| 5,013,311 A * | 5/1991 | Nouri | | 606/4 |
| 5,088,803 A * | 2/1992 | Buzawa | | 385/33 |
| 5,334,191 A | 8/1994 | Poppas et al. | | |
| 5,815,627 A | 9/1998 | Harrington | | |
| 6,144,787 A | 11/2000 | Johnston et al. | | |
| 6,267,779 B1 | 7/2001 | Gerdes | | |
| 6,438,302 B1 * | 8/2002 | Utsui et al. | | 385/117 |
| 7,988,688 B2 * | 8/2011 | Webb et al. | | 606/13 |

FOREIGN PATENT DOCUMENTS

WO    WO 2007106075 A2 *   9/2007

* cited by examiner

*Primary Examiner* — William Thomson
*Assistant Examiner* — Sebastian X Lukjan
(74) *Attorney, Agent, or Firm* — Morrison & Foerster LLP

(57) ABSTRACT

Laser treatment apparatus includes one diode-laser providing infrared radiation for the treatment and another diode-laser for providing visible radiation. A lens launches the infrared and visible radiations from the diode-lasers into the entrance face of the optical fiber for transporting the radiations to a treatment location.

17 Claims, 2 Drawing Sheets

LENSED DUAL-CHIP FIBER-COUPLER FOR PROVIDING AN AIMING BEAM IN AN INFRARED RADIATION DELIVERY APPARATUS

TECHNICAL FIELD OF THE INVENTION

The present invention relates in general to apparatus for delivering, via and optical fiber, near infrared (NIR) radiation for medical or dental procedures. The invention relates in particular to a method of providing a visible aiming-beam in such an apparatus.

DISCUSSION OF BACKGROUND ART

NIR radiation from a diode-laser is used in medical and dental treatments and procedures. In certain procedures the infrared radiation is used to cut or cauterize tissue. Such procedures include laser soft tissue curettage and laser removal of diseased or infected tissue within the periodontal pocket. In this and any other such procedure an operator must be certain that the NIR radiation will be delivered precisely to a location on tissue where the procedure is required. One way to ascertain this is to provide the delivery apparatus, typically a hand-held (handpiece) apparatus, with a visible aiming beam.

One method of providing an aiming beam for an NIR delivery handpiece is described in U.S. Pat. No. 6,144,787 granted to Johnston et al. Here, the NIR radiation is transported to the handpiece, from a diode-laser remote from the handpiece, via an optical fiber. A collar of a translucent material surrounds the fiber within the handpiece. The translucent collar is illuminated by light from three red-light-emitting diodes (LEDs). The handpiece includes lens elements arranged to focus the NIR radiation and scattered red light from an end of the translucent collar at a predetermined distance from the handpiece. The NIR radiation is focused to a circular spot, with the red light focused into an annulus surrounding the circular spot.

A drawback of the Johnston et al. handpiece arrangement is that the LEDs have a relatively low brightness compared, for example, with a diode-laser. This low brightness, coupled with the fact that only a fraction of the total light output of the LEDs is actually focused into the circle, means that the circle has less than optimum brightness and can be difficult to see in bright ambient light conditions. There is a need for a means of providing a brighter aiming beam for IR delivery apparatus.

SUMMARY OF THE INVENTION

In one aspect of the present invention, optical apparatus comprises first and second diode-lasers spaced apart from each other in a slow-axis direction of the diode-lasers and an optical fiber having an entrance face. The first diode-laser is arranged to emit first a beam of radiation having an infrared wavelength and the second diode-laser is arranged to emit a second beam of radiation having a visible wavelength. A lens is arranged to launch the infrared and visible radiation from the diode-lasers into the entrance face of the optical fiber.

In a preferred embodiment of the apparatus the diode-lasers the lens and the optical fiber are configured and arranged such that the infrared radiation has a launch numerical aperture (NA) at the optical fiber less than the launch NA of the visible radiation. The launch NA of the infrared radiation is selected such that primarily low order modes thereof propagate in the optical fiber and the launch NA of the visible radiation is selected such that primarily high order modes thereof propagate in the optical fiber. The optical fiber has a length selected such that the infrared radiation leaves the optical fiber with an about circularly symmetrical centrally weighted intensity distribution, and the visible radiation leaves the optical fiber with a an about circularly symmetrical annularly weighted intensity distribution.

BRIEF DESCRIPTION OF THE DRAWINGS

The accompanying drawings, which are incorporated in and constitute a part of the specification, schematically illustrate a preferred embodiment of the present invention, and together with the general description given above and the detailed description of the preferred embodiment given below, serve to explain principles of the present invention.

DETAILED DESCRIPTION OF THE INVENTION

Figure 1:
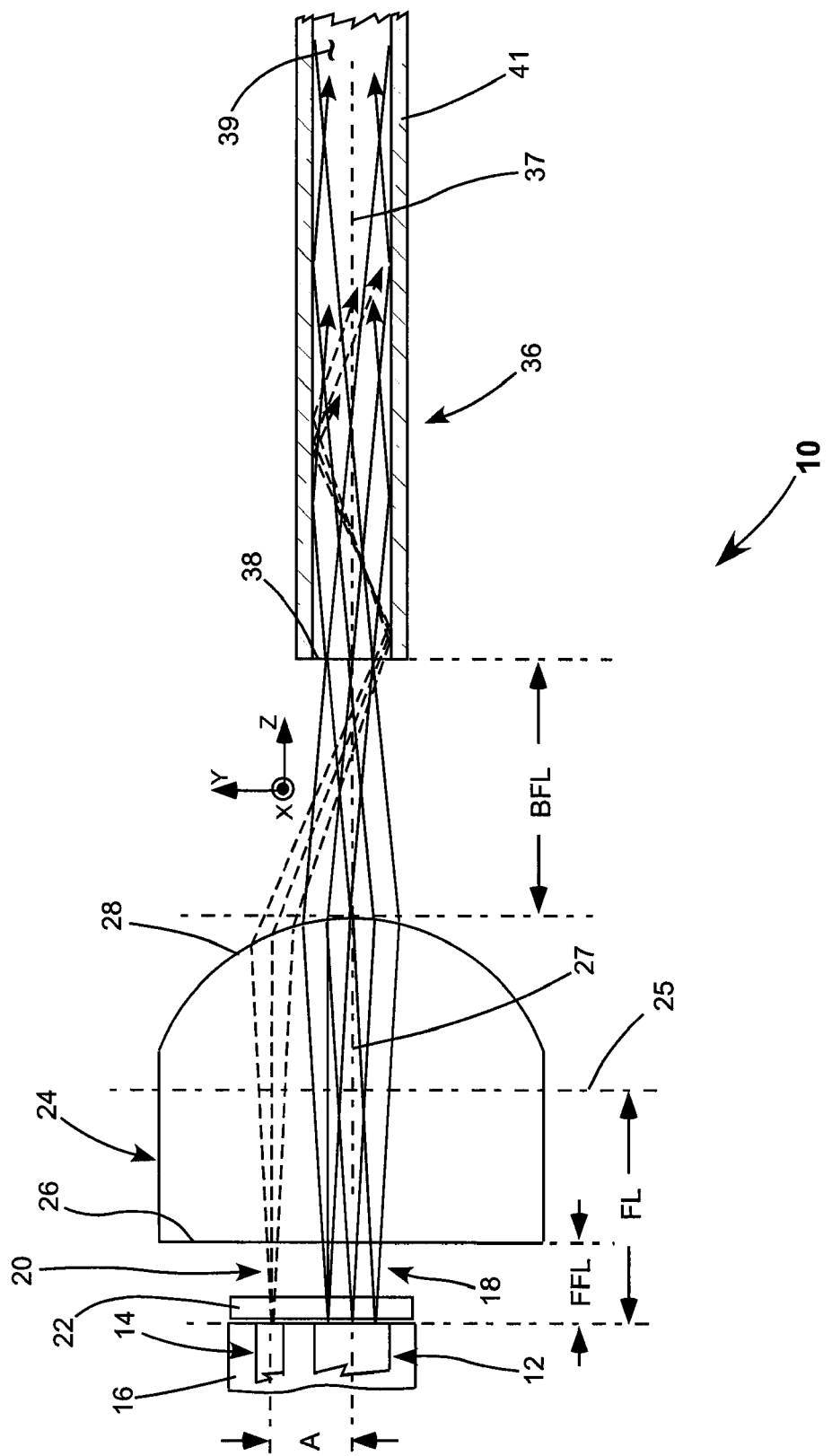
FIG. 1 schematically illustrates one preferred embodiment of NIR radiation delivery apparatus in accordance with the present invention including one diode-laser delivering NIR radiation and another diode-laser delivering visible radiation, with the output of both of the diode-lasers being launched by a single lens into an entrance face of a length of optical fiber having a longitudinal axis aligned with the optical axis of the lens and the emission axis of the infrared-delivering diode laser.

Referring now to the drawings, wherein like components are designated by like reference numerals, FIG. 1 schematically illustrates a preferred embodiment 10 of infrared radiation delivery apparatus in accordance with the present invention. Apparatus 10 includes a diode-laser 12 for generating NIR radiation, for example, radiation having a wavelength of 940 nanometers (nm). The diode-laser is preferably a high power (wide stripe) multi-mode diode-laser having an output power of about 5 Watts (W) pulsed or greater, of 3 W CW or greater. Apparatus 10 also includes a diode-laser 14 for generating visible radiation. Laser 14 is preferably a single-mode or few mode (narrow stripe) diode-laser providing radiation at a visible wavelength of about 635 nm. This radiation is intended to provide a visual indication. Lasers 12 and 14 are mounted on a common heat sink 16 with slow-axes thereof aligned. The diode-lasers are spaced apart in the slow-axis direction by a distance A with emitting faces thereof aligned in the slow axis.

Apparatus 10 is characterized in the drawing by Cartesian axes X, Y, and Z where Z is the propagation or delivery axis direction, transverse axis Y corresponds to the slow-axis of the diode-lasers, and transverse axis X corresponds to the fast-axis of the diode-lasers. Radiation beams 18 and 20 from diode-lasers 14 and 16, respectively, are collimated in the fast-axis by a collimating lens 22 having optical power in the fast-axis (X-axis) only. The beams continue to diverge in the slow-axis (Y-axis). A thick lens 24 has a plane entrance face 26 and a (spherical) convex exit face 28. Lens 24 has an optical axis 27 and has a focal length FL, here, shown measured from a first principle plane 25. Surface 26 of the lens is located a front focal length (FFL) of the lens away from diode-lasers 12 and 14, i.e. the lasers are located a focal length (FL) away from plane 25 of lens 24. Optical axis 27 of lens 24 is aligned with the propagation axis of diode-laser 12, defined as extending from the center of the emitting aperture of diode-laser 12.

An optical fiber 36 (only a proximal end of which is depicted in FIG. 1) has a core 39 and a cladding 41, and has an entrance face 38. Fiber 36 has a longitudinal axis 37 which is aligned, at entrance face 38 thereof (here, of course, recognizing that fibers can bend), with optical axis 27 of lens 24. This fiber is intended to transport radiation from diode-laser 12 (designated by solid lines) to a location where the radiation will be is used for whatever treatment is intended. Visible radiation from diode-laser 14 designated by dashed-lines, is used to provide an indication of where NIR radiation delivered from the fiber is incident at the treatment location.

Entrance face 38 of fiber 36 is located (on the Z-axis) a back focal length (BFL) from lens 24. The means that diode-laser laser emitters, the lens and the fiber entrance face are arranged in a manner commonly referred to as an F-F optical system by practitioners of the art. In an ideal case of an aberration-free system, diverging ray bundles for any point in an emitter face would be collimated by the lens into the entrance face of the optical fiber. In the arrangement of FIG. 1 this is true for ray bundles from diode-laser 12 as these rays are relatively close to the axis. NIR radiation exiting the fiber will have the same numerical aperture (NA) as the NIR radiation entering (launched) into the fiber.

Preferably, the launch NA of the NIR radiation is sufficiently low, for example less than about 0.15, such that only low order modes are excited in the fiber and the NIR radiation is delivered from the fiber with a centrally weighted intensity distribution after being homogenized by transmission through the fiber. The launch NA of the visible radiation from diode-laser 14 is preferably high enough, for example greater than about 0.25, that the visible radiation excites primarily high order modes of the fiber. This causes the visible radiation to exit the fiber in a annular weighted or "doughnut" mode surrounding the NIR radiation. The acceptance NA of the fiber should, of course, be high enough to support the high launch NA of the visible radiation.

The relatively high launch NA of the visible radiation is provided by the slow-axis displacement A of diode-laser 14 from diode laser 12. As rays 20 from diode-laser 14 are incident on convex surface 28 of lens 24 relatively far off-axis, there is aberration, and the rays are not exactly collimated. The rays actually converge, which facilitates delivery thereof into the fiber. As this radiation is not treatment-critical, the aberration is tolerable.

In the F-F system arrangement of FIG. 1, the launch NA of the NIR radiation beam (the main beam) is given by an equation:

$$NA = W/2F \qquad (1)$$

where W is the beam-width leaving the diode-laser, i.e., the emitter width or stripe width, and F is the focal length (FL) of lens 24. In one preferred example, lens 24 has a focal length of about 0.8 millimeters (mm) and diode-laser 12 has an emitter width of about 130 micrometers (μm). This provides that the launch NA of NIR radiation entering fiber 36 is about 0.08. In this example, a preferred value for spacing A of diode-lasers 12 and 14 is about 250 μm.

A significant advantage of this arrangement is that, as is evident from equation (1), the launch NA of the radiation entering fiber 36 and correspondingly of the radiation delivered from fiber 36 is independent of the slow-axis divergence and NA of radiation delivered from (the emitting face of) diode-laser 12.

Those skilled in the art will recognize that the slow-axis NA and divergence angle of a diode-laser beam is a relatively sensitive function of current passed through the diode-laser, and that varying the current is the means by which the power of radiation delivered by the diode-laser can be varied. In one example of a diode-laser suitable for diode-laser 12, increasing current from 1.0 Ampères (A) to 3.0 A, changed the emitter NA from about 0.05 to about 0.08, and the divergence angle from about 4.5° to 6.8°. In the usual prior-art coupling scheme wherein a diode-laser emitter is focused (imaged) onto the entrance face of a fiber, such current-dependent changes would create corresponding changes in the launch NA of radiation entering the fiber.

The length of fiber 36 is preferably be sufficiently long that radiation entering the fiber is homogenized by transport along the fiber. NIR radiation enters the fiber with an elongated radiation cross-section with different NA in the fast axis different from that in the slow axis. Homogenization is required such that the NIR radiation exits the fiber with a circularly symmetrical intensity distribution. Homogenization also provides that the visible radiation exits the fiber in a doughnut mode with an about rotationally symmetrical annularly weighted intensity distribution. In the example discussed above, with a fiber core diameter of about 200 μm, a fiber length of about 36 mm has been found to provide adequate homogenization of the NIR and visible radiation.

A further advantage of the F-F arrangement described for coupling radiation into the optical fiber is that a certain "tuning" (selective variation) range is possible for the launch NA, and accordingly the exit NA of the NIR radiation. A description of such NA tuning is set forth below with reference to FIG. 2.

Figure 2:
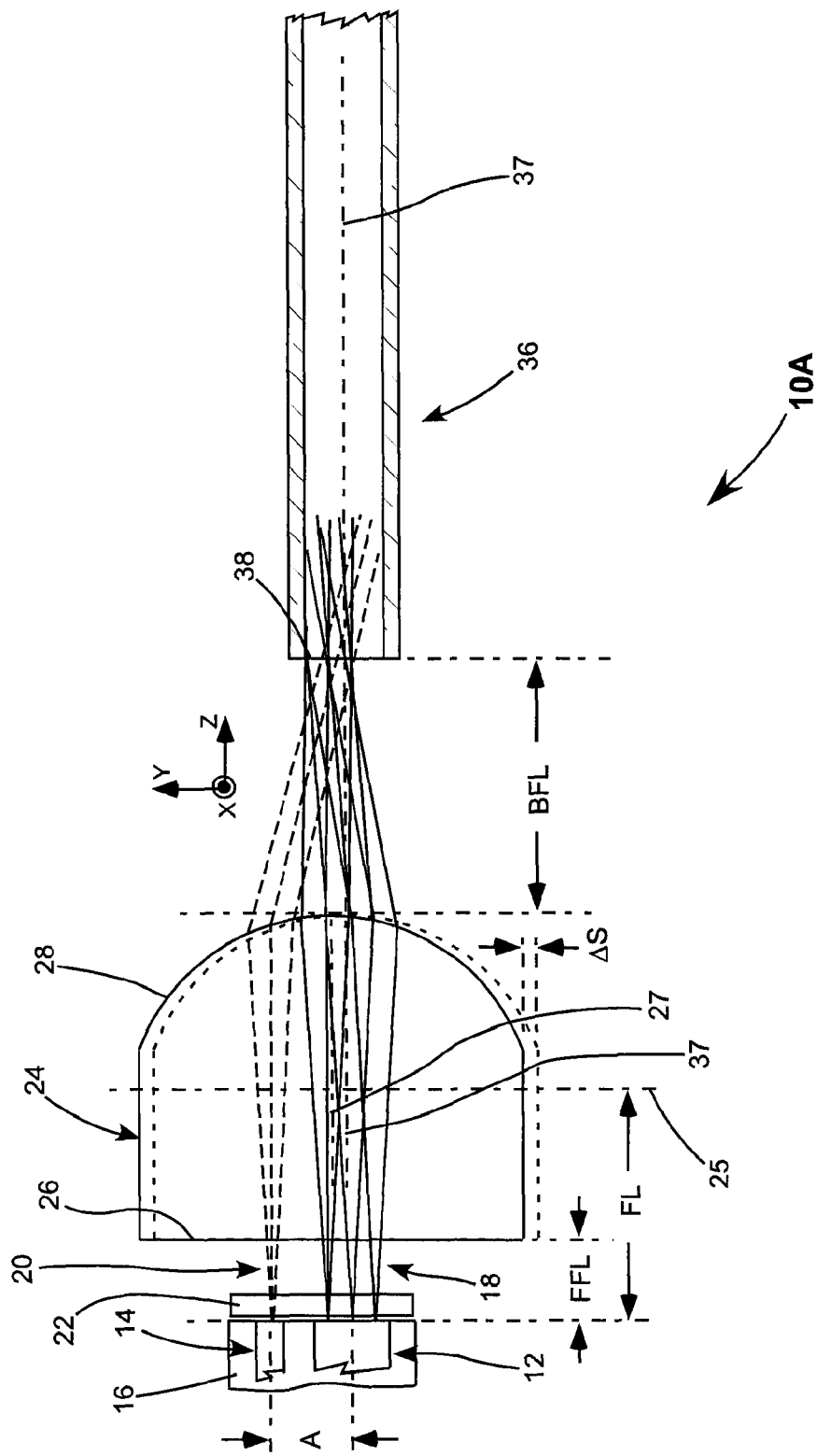
FIG. 2 schematically illustrates another preferred embodiment of NIR radiation delivery apparatus in accordance with the present invention similar to the apparatus of FIG. 1, but wherein the optical axis of the lens is displaced in the slow-axis direction of the diode-laser from the longitudinal axis of the optical fiber and the emission axis of the infrared-delivering diode-laser.

Here, apparatus 10A is similar to apparatus 10 of FIG. 1 with an exception that lens 24 in apparatus 10A is displaced in the Y-axis by a distance ΔS from the on-axis position of apparatus 10 (indicated by a dotted outline in FIG. 2). This misaligns the fiber axis 37 and the lens axis 27 by the same amount. A pre-requisite for this is that core 39 of fiber 36 must have a diameter larger than the maximum dimension of NIR radiation at entrance face 38 of the fiber. With this displacement, the launch NA of the fiber would be approximated as follows:

$$NA \approx W/2F + \Delta S/F \qquad (2)$$

In the example discussed the maximum dimension of NIR radiation on face 38 would be about 140 μm. A core diameter of 200 μm would allow a displacement of ±0.03 mm, that being one-half of the difference between the beam dimension and the core dimension. It should be noted that the launch NA of the NIR radiation will increase whether the lens is displaced toward or away from diode-laser 14. Accordingly with this 0.03 mm-displacement, the tuning range for the NA would be from about 0.08 to about 0.12. In the illustrated example wherein the lens is displaced toward diode-laser 14 the launch NA of the visible radiation decreases from the on-axis value. Were the lens displaced in an opposite direction, the launch NA of the visible radiation would increase from the on-axis value. When using this NA tuning technique, care should be taken not to increase the NA of the NIR radiation to a value which would cause the onset of donut modes or increase the value of the visible NA to a value higher than the acceptance NA of the fiber.

The present invention is described above with reference to particular examples of preferred embodiments of the invention. Based on the description one skilled in the art may devise other embodiments and examples of the invention without departing from the spirit and scope of the invention as defined by the claims appended hereto.

What is claimed is:

1. Optical apparatus used for dental and medical procedures, comprising:

first and second diode-lasers, the first diode-laser arranged to emit a first beam of radiation having an infrared wavelength and the second diode-laser arranged to emit a second beam of radiation having a visible wavelength;

an optical fiber having a core surrounded by a cladding and an entrance face and an exit face; and a lens arranged to launch the infrared and visible radiation from the diode-lasers into the core of the optical fiber through the entrance face thereof the optical fiber and wherein the propagation axis of the second beam is spaced from the optical axis of the lens a distance greater than the spacing between the propagation axis of the first beam and the optical axis of the lens so that the launch numerical aperture of the second beam as the second beam enters the optical fiber is greater than the launch numerical aperture of the first beam, so that the second beam excites higher order modes in the fiber compared to the first beam and wherein the optical fiber has a length selected such that the visible radiation leaves the exit face with a circularly symmetrical annularly weighted intensity distribution.

2. The apparatus of claim 1, wherein the infrared radiation is launched into the optical fiber at a predetermined first launch numerical aperture selected such that primarily low order modes thereof propagate in the optical fiber.

3. The apparatus of claim 2 wherein the first launch numerical aperture is less than 0.15.

4. The apparatus of claim 1 wherein the beam of radiation emitted by the first diode-laser has a beam divergence and a beam numerical aperture which vary dependent on the magnitude of electrical current passed through the diode-laser to energize the diode-laser, and wherein the lens and the entrance face of the optical fiber are configured and arranged such that the launch numerical aperture of the infrared radiation is independent of variation of the divergence and numerical aperture of the emitted infrared-radiation beam.

5. The apparatus of claim 4, wherein the first diode-laser is spaced apart from the lens by about a back focal length of the lens and the lens is spaced apart from the entrance face of the optical fiber by about a front focal length of the lens.

6. The apparatus of claim 1, wherein the visible radiation is launched into the optical fiber at a predetermined second launch numerical aperture selected such that primarily high order modes thereof propagate in the optical fiber.

7. The apparatus of claim 6, wherein the second launch numerical aperture is greater than 0.26.

8. Optical apparatus used for dental and medical procedures, comprising: first and second diode-lasers spaced apart from each other in a slow-axis direction of the diode-lasers, the first diode-laser arranged to emit a first beam of radiation having an infrared wavelength and the second diode-laser arranged to emit a second beam of radiation having a visible wavelength; an optical fiber having a core surrounded by a cladding and an entrance face and an exit face; a lens arranged to launch the infrared and visible radiation from the diode-lasers into the core of the fiber through the entrance face thereof the optical fiber; and wherein spacing between the diode lasers causes the propagation axis of the second beam to be spaced from the optical axis of the lens a distance greater than the spacing between the propagation axis of the first beam and the optical axis of the lens so that the launch numerical aperture of the second beam as the second beam enters the optical fiber is greater than the launch numerical aperture of the first beam, so that the second beam excites higher order modes in the fiber compared to the first beam and wherein the optical fiber has a length selected such that the visible radiation leaves the exit face with a circularly symmetrical annularly weighted intensity distribution.

9. The apparatus of claim 8, wherein the launch numerical aperture of the first beam is determined by the width of the infrared radiation beam leaving the diode-laser and the focal length of the lens and the launch numerical aperture of the second beam is dependent on the slow-axis spacing between the first and second diode-lasers and the focal length of the lens.

10. The apparatus of claim 8 wherein the launch numerical aperture of the first beam less than 0.15 and the launch numerical aperture of the second beam is greater than 0.25.

11. The apparatus of claim 10, wherein the launch numerical aperture of the first beam is selectable between a minimum value and a maximum value.

12. The apparatus of claim 11, wherein the first diode-laser is spaced apart from the lens by about a back focal length of the lens and the lens is spaced apart from the entrance face of the optical fiber by about a front focal length of the lens.

13. The apparatus of claim 12, wherein the minimum value of the launch numerical aperture of the first beam is selected by aligning the propagation axis of the first diode-laser, the optical axis of the lens and the longitudinal axis of the fiber, and wherein a higher value of the launch numerical aperture of the first beam is selected by misaligning, in the slow-axis direction of the diode-laser, the optical axis of the lens with respect to the aligned propagation axis of the diode-laser and the longitudinal axis of the optical fiber.

14. The apparatus of claim 13, wherein the infrared radiation has a maximum beam-cross-section dimension at the entrance face of the optical fiber and the optical fiber has a core diameter greater than this maximum beam-cross-section dimension, and wherein the maximum value of the launch numerical aperture of the first beam is selected when the misalignment of the optical axis of the lens is equal to one-half the difference between the maximum beam-cross-section dimension of the infrared radiation at the entrance face of the diode-laser and the core diameter of the optical fiber.

15. A device used for dental and medical procedures and for delivering an infrared and a visible beam of radiation comprising: a support; a first diode laser mounted on said support and generating an infrared radiation beam having a fast axis and a slow axis both mutually perpendicular to the propagation axis of the beam; a second diode laser mounted on said support and spaced from the first diode laser in a direction of said slow axis, said second diode laser generating a visible beam having a fast and slow axis, with the fast axis of the first diode laser being parallel to the fast axis of the second diode laser; an optical fiber having a core surrounded by a cladding and an entrance face spaced from and aligned with the first diode laser, said fiber further including an exit face: and a single, common focusing lens located between the diode lasers and the optical fiber, with the optical axis of the lens being substantially aligned with the propagation axis of the beam from the first diode laser such that the radiation from the first diode laser is launched into the core of the fiber with a first numerical aperture that results in propagation through the fiber in substantially lower order modes while the radiation from the second diode laser is launched into the core of the fiber with a second numerical aperture greater than the first numerical aperture that results in propagation through the fiber in higher order modes and wherein the optical fiber has a length selected such that the visible radiation leaves the exit face with a circularly symmetrical annularly weighted intensity distribution.

16. The apparatus of claim 15 wherein the first numerical aperture is less than 0.15 and the second numerical aperture is greater than 0.25.

17. The apparatus of claim 1 wherein first and second diode-lasers are spaced apart from each other in a slow-axis direction of the diode-lasers and wherein the spacing causes the beams from the diode-lasers to propagate within the lens at different locations with respect to the optical axis thereof.

* * * * *